United States Patent [19]

Heil

[11] Patent Number: 4,837,862
[45] Date of Patent: Jun. 13, 1989

[54] SUN, RAIN AND WIND DEFLECTOR

[76] Inventor: Dean Heil, 16441 Creeksouth, Houston, Tex. 77068

[21] Appl. No.: 49,857

[22] Filed: May 12, 1987

[51] Int. Cl.$^4$ ............................ A61F 9/04; A42B 1/18
[52] U.S. Cl. .............................................. 2/12; 2/433; 2/454; 351/123
[58] Field of Search ................... 2/433, 12, 9, 13, 432, 2/426, 206, 209.3, 454, 15; 351/123, 46

[56] References Cited

U.S. PATENT DOCUMENTS

| | | | |
|---|---|---|---|
| 1,533,506 | 4/1925 | Mann | 351/123 |
| 1,585,023 | 5/1926 | Fant | 2/12 X |
| 2,139,275 | 12/1938 | Lee | 2/433 X |
| 2,406,190 | 8/1946 | Burdick | 2/433 |
| 3,614,216 | 10/1971 | Rosenthal | 2/454 X |
| 3,932,031 | 1/1976 | Johnston | 2/13 X |
| 4,251,302 | 2/1981 | Leonard et al. | 351/123 X |
| 4,649,908 | 3/1987 | Ghaly | 2/15 X |

FOREIGN PATENT DOCUMENTS

| | | | |
|---|---|---|---|
| 0285971 | 4/1914 | Fed. Rep. of Germany | 2/433 |
| 1024606 | 1/1953 | France | 2/433 |
| 0477020 | 6/1953 | Italy | 2/12 |

*Primary Examiner*—Peter Nerbun
*Attorney, Agent, or Firm*—Mark G. Bocchetti; Bernard A. Reiter

[57] ABSTRACT

Disclosed is a personal sun shield device for attachment directly to the facial area of the wearer. The shield has a primary shield member preferrably positionable immediately above the wearer's line of vision and a lower shield member which extends downward from the primary shield member to provide a slot such that the wearer's line of vision is through the slot between the primary shield member and the lower shield member. The lower shield member can be folded upward to reside in abutting position immediately behind the primary shield member so that the wearer has the option of using or not using the lower shield member. The primary shield member attaches to the face of the wearer by means of suction cups or two-sided tape preferrably in the area of the wearer's temples. This direct attachment allows the wearer to manipulate the primary shield member slightly upward or downward by means of merely raising or lowering his brow. The attachment means are mounted to support members which connect to the primary shield member in a hinge fashion. This allows the positioning of the primary shield member to and about the face of the wearer such that the hinged connections become the furthermost ends of the shield device when the shield is worn. This hinged connection of the attachment means reduces the amount of stress placed on the attachment means when the shield is being worn, thus preventing the flexible nature of the primary shield from prying the attachment means from the facial area of the wearer.

10 Claims, 2 Drawing Sheets

U.S. Patent   Jun. 13, 1989   Sheet 2 of 2   4,837,862
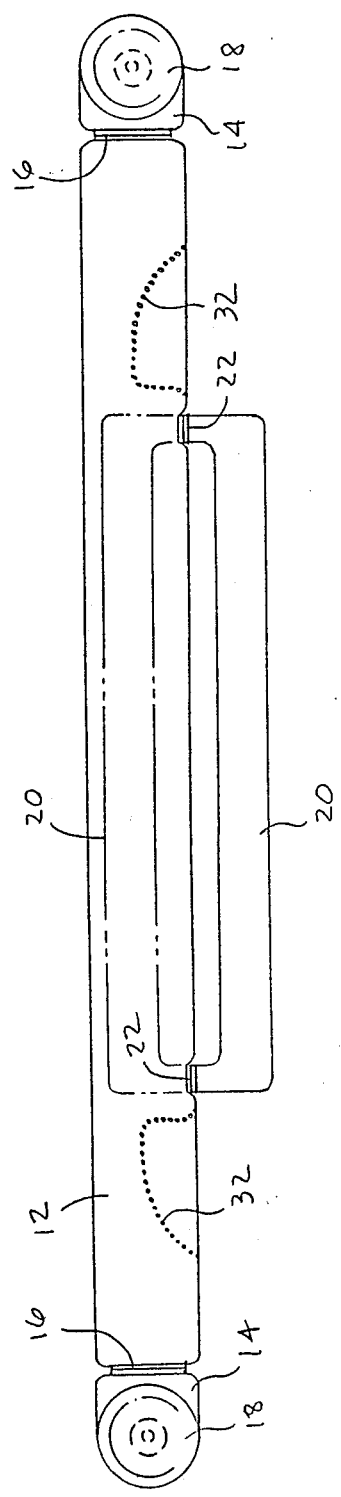
FIG. 2
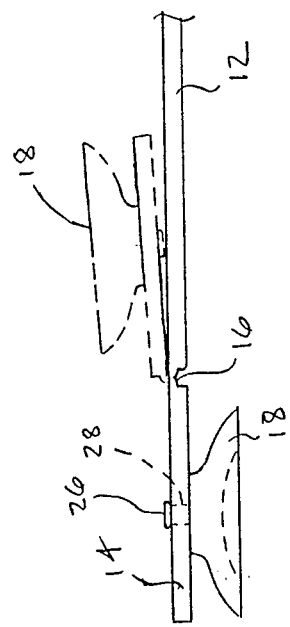
FIG. 3
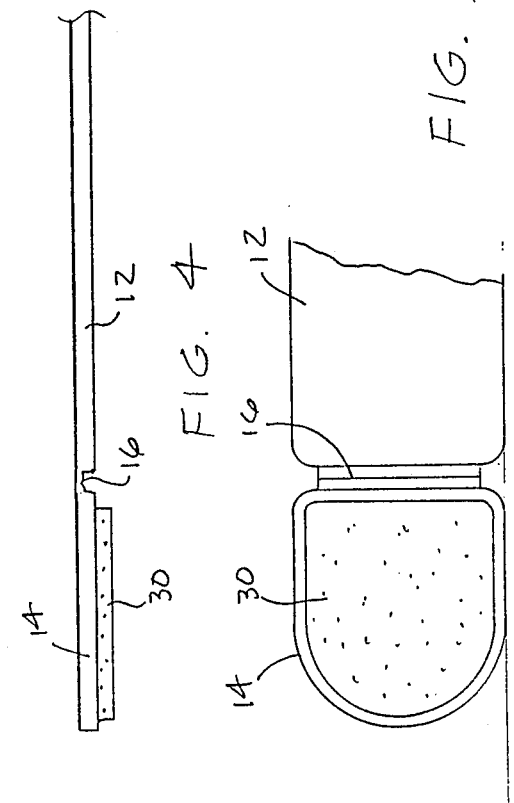
FIG. 4
FIG. 5

SUN, RAIN AND WIND DEFLECTOR

BACKGROUND OF THE INVENTION

1. Field of the Invention

The present invention relates generally to shields and deflectors and more particularly to shields and deflectors which attach directly to the face of the wearer for protecting the eyes of the wearer from the sun.

2. Brief Description of the Prior Art

There are a number of personal eye shade and shield devices in the prior art. One such eye shade can be found in U.S. Pat. No. 2,710,966 to Dale, Jr. The Dale, Jr. eye shade is designed to abut directly against the forehead of the user and is held in place by means of members extending back to the ears of the wearer or by means of an elastic band which extended about the head of the wearer. Although Dale, Jr. taught an eye shade having upper and lower shield portions for protection both above and below the line of sight of the wearer, such upper and lower portions are in fixed position with regard to each other. Therefore, the shield of Dale, Jr. requires the simultaneous use of the upper and lower shield portions. Further, due to the enclosing structure and close abutment with the face of the wearer, the Dale, Jr. eye shade is not adaptable for use by a person who would desire to use the shade in conjunction with eye glasses.

Another eye shield having similar deficiencies as those of the Dale, Jr. patent can be found in U.S. Pat. No. 2,714,716 to McLennan. As with Dale Jr., McLennan teaches an eye shield having upper and lower shields which are in fixed relationship to one another. Arms are provided which extend back to the ears of the wearer to support the shield. The McLennan shield is also not adaptable for use with eye glasses.

Still another eye shade of the prior art is depicted in U.S. Pat. No. 2,645,774 to Dale, Jr. The support means for this Dale, Jr. eye shade are arms which extend back to the ears of the wearer. Again, the upper and lower shield portions reside in fixed position with regard to one another and therefore, when worn, both the upper and lower portions of the shield must be used.

Italian Pat. No. 473,263 to Savoini, et al apparently teaches a shield designed to mount to a pair of eye glasses made specifically for that purpose. The shield extends outward from the eye glasses and can be pivoted to a variety of positions. The Savoini, et al device is supported by typical eye glass arms which extend back to the ears of the wearer. Savoini does not teach a combination of upper and lower shields such that the wearer can sight between the two shields.

Nothing in the prior art teaches a shield which mounts directly to the face of the wearer by means of suction cups or two sided tape. Nothing in the prior art teaches a shield which raised or lowered by the wearer merely by raising or lowering his or her brow. Further, nothing in the prior art teaches the use of a lower shield member which can be folded down to allow the wearer to sight between the upper and lower shield members or to be folded upward behind the upper shield such that the wearer has the choice of using the upper shield alone or in combination with the lower shield.

SUMMARY OF THE INVENTION

Accordingly, it is an object of the present invention to provide a sun deflector or shield which attaches directly to the face of the wearer.

Another object of the present invention is to provide a sun deflector which can be raised or lowered by the wearer by the action of raising or lowering his brow.

A further object of the present invention is to provide a sun deflector which has a fold-down lower shield member such that the wearer has the option of using the upper shield member alone or in combination with the lower shield member.

Yet another object of the present invention is to provide a sun deflector which can be used in conjunction with and without interference from a pair of eye glasses.

Briefly stated, the foregoing and numerous other features, objects and advantages of the present invention will become readily apparent upon a reading of the detailed description, claims and drawings set forth hereinafter. These features, objects and advantages are accomplished through the use of a flexible shield member having attachment means for mounting directly to the face of the wearer extending from each end of the flexible shield member. The attachment means may be in the form of suction cups or two-sided tape. In such manner, the attachment means are positioned to affix at the temple area of the face of the wearer. A lower shield member is provided which attaches to and extends downward from the main shield member. A slot is provided between the main shield member and the lower shield member when the lower shield member is to be used. This allows the wearer to position the shield such that his line of vision is through the slot between the main shield member and the lower shield member. When the wearer does not desire to use lower shield member, it may be folded up in abutting position behind the upper shield member such that it does not interfere in any way with the vision of the wearer.

The wearer can position the shield at a variety of angles with respect to his line of vision by repositioning the attachment means to place the shield at a different angle or, in the case of the suction cup attachment means, pivoting the main shield member about the suction cups. When the shield of the present invention is being worn, the wearer maintains some control of the position of the shield without having to manipulate the shield with his or her hands. Because the shield attaches to the area directly to the temples of the wearer, the wearer can raise and lower the shield merely by raising or lowering his or her brow in the normal manner.

Cut-outs are provided in the shield in the area of the shield which would reside in close proximity to the sides of the wearer's face. These cut-outs provide an area for the arms of a pair of eye glasses to reside such that the shield can be used by a person who wears glasses without interference to either the shield or the glasses.

BRIEF DESCRIPTION OF THE DRAWINGS

FIG. 2 is a plan view of the shield of the present invention.

FIG. 3 is a top view of the shield of the present invention using suction cup attachment means.

FIG. 4 is a top view of one end of the present invention using two sided tape as the attachment means.

FIG. 5 is a side elevation of the hinged end of the present invention using two-sided tape as the attachment means.

DETAILED DESCRIPTION OF THE PREFERRED EMBODIMENT

Figure 1:
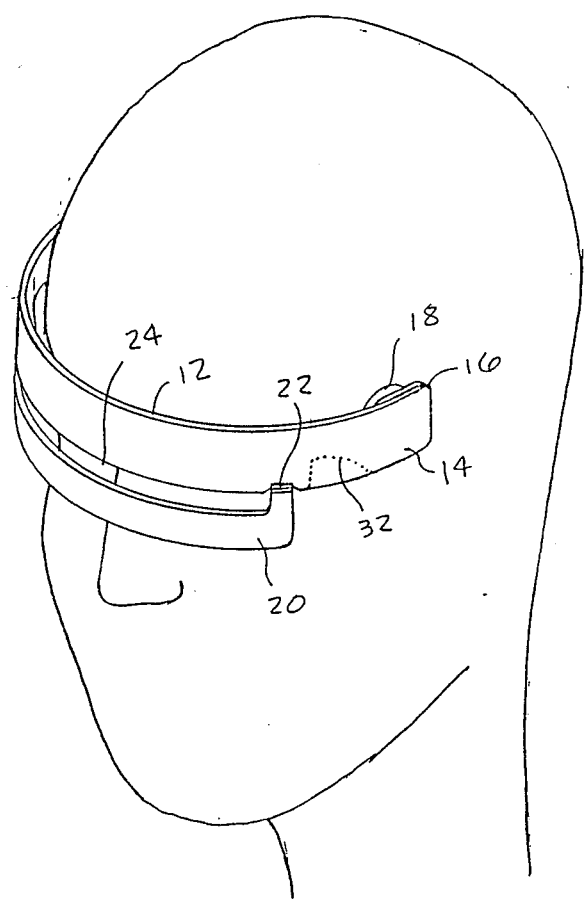
FIG. 1 is a perspective view of the shield of the present invention mounted to the face of the wearer.

Turning now to the figures, there is shown in FIG. 1 the flexible shield 10 of the present invention. Shield 10 includes a primary shield member 12. At each end of primary shield member 12 is a support member 14. Support member 14 are connected to primary shield member 12 by means of hinge 16. Mounted to support members 14 are suction cups 18. Suction cups 18 are used to attach the shield 10 to that area of the wearer's face at the temples.

Attached to primary shield member 12 is lower shield member 20. Lower shield member 20 attaches to primary shield member 12 by means of hinges 22. As shown in FIG. 1, when lower shield member 20 is in its operable position, there is a slot 24 between lower shield member 20 and primary shield member 12. The wearer's line of vision is through slot 24.

The shield 10 of the present invention can be used with lower shield member 20 in nonoperable position such that it is folded upward using hinges 22 to reside in parallel and abutting position behind primary shield member 12.

Support members 14 fold under primary shield member 12 by means of hinge 16 such that when the shield 10 is mounted to the face of the wearer as best shown in FIG. 1, support members 14 reside behind primary shield member 12. Suction cups 18 mount to support members 14 preferably by means of nipple 26 which extends from suction cup 18 through bore 28 in support member 14. An alternative means of attaching shield 10 of the present invention to the face of the wearer is shown in FIGS. 4 and 5. The suction cup 18 is replaced with two sided tape 30. The exposed face of two sided tape 30 is covered with a reusable adhesive material such that it may be applied to and removed from human skin for multiple use before requiring additonal adhesive or replacement of the two sided tape 30.

When the shield 10 of the present invention is attached to the wearer's face just above the area of the temples of the face of the wearer either by means of suction cups 18 or by means of two sided tape 30, the wearer can control the position of the primary shield member 12 with respect to his line of vision. The points of connection directly to the wearer's face allows the wearer to raise or lower primary shield member 12 merely by raising or lower his brow.

Primary shield member 12 is provided with cut-outs 32. Cut-outs 32 are outlined by perforations or a perforated seam. If the wearer of the shield desires to use it in conjunction with a pair of eye glasses he need only remove cut-outs 32. Through the use of cut-outs 32, the shield 10 of the present invention can be used with eye glasses. The primary shield member 12 wraps about the face of the wearer and extends away from the face of the wearer such that eye glasses can be worn with the shield 10 being further from the face of the wearer than the plane of the eye glasses. The ears which support the eye glasses pass through cut outs 32 such that the eye glasses and shield 10 do not interfere with one another.

From the foregoing, it will be seen that this invention is one well adapted to attain all of the ends objects hereinabove set forth, together with other advantages which are obvious and which are inherent to the device.

Preferably, primary shield member 12, lower shield member 20, support members 14, hinges 22 and hinges 16 are all constructed from a single piece of opaque, flexible, plastic-like material or from a stiff paper for temporary or disposable type use. Hinges 16 and hinges 20 are preferrably of lesser thickness than primary shield member 12, lower shield member 20 and support members 14 thereby creating lines for the desired folding and hinge-like action.

It will be understood that certain features and subcombinations are of utility and may be employed with reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A personal sun shield comprising:
  (a) a flexible primary shield member extending about the face of the wearer;
  (b) a lower shield member extending downward from said primary shield member such that a slot is provided between said primary shield member and said lower shield member at the wearer's line of vision;
  (c) hinge means connecting said primary shield member to said lower shield member, said hinge means allowing said lower shield member to be folded upward to reside behind and become contiguous with said primary shield member.

2. A personal sun shield comprising:
  (a) a flexible primary shield member having two ends, said primary shield member extending about and away from the face of a wearer at a position above the wearer's line of vision;
  (b) attachment means located at each of said ends of said primary shield member for affixing said primary shield member directly to the brow and temple area of the wearer, such that said primary shield member forms an arcuate cantilever; and
  (c) means for allowing the wearer to raise and lower said flexible primary shield member by control of facial muscles.

3. A personal sun shield as recited in claim 2 wherein: said attachment means are suction cups.

4. A personal sun shield as recited in claim 2 wherein: said attachment means are strips are two-sided adhesive tape.

5. A personal sun shield as recited in claim 1 further comprising:
  cut-out portions in said primary shield member so that said primary shield member can be worn in conjunction with a pair of eye glasses.

6. A personal sun shield as recited in claim 2 further comprising:
  a plurality of hinged connections connecting said attachment means to said primary shield member, said hinged connections residing rewardmost from the face of the wearer.

7. A personal sun shield comprising:
  (a) a light weight flexible primary shield member, said primary shield member being substantially elongated and planar in configuration and having two ends,
  (b) a support member located at each of said ends allowing said primary shield member to extend about and away from the face of a wearer without any intermediate support provided to said primary shield member between said support members;

(c) means for affixing said support members to the brow and temple area of the wearer and for allowing the wearer to raise and lower said flexible primary shield by control of facial muscles.

8. A personal sun shield as recited in claim 6 further comprising:

a plurality of support members to which said attachment means are affixed, said support members being connected to said primary shield member by said hinged connections, said hinged connections allowing said support members to pivot toward each other so that said attachment means face each other when affixed to the face of the wearer.

9. A personal sun shield as recited in claim 2 further comprising:

a lower shield member extending downward from said primary shield member such that a slot is provided between said primary shield member and said lower shield member at the wearer's line of vision.

10. A personal sun shield as recited in claim 9 further comprising:

hinge means connecting said primary shield member to said lower shield member, said hinge means allowing said lower shield member to be folded upward to reside in abutting position contiguous with said primary shield member.

* * * * *